United States Patent [19]

Tokoyama

[11] Patent Number: 5,074,158
[45] Date of Patent: Dec. 24, 1991

[54] POWDER GRANULE SAMPLE INSPECTION APPARATUS

[75] Inventor: Katsumi Tokoyama, Osaka, Japan

[73] Assignee: Hajime Industries Ltd., Tokyo, Japan

[21] Appl. No.: 562,678

[22] Filed: Aug. 3, 1990

[51] Int. Cl.$^5$ ............................................. G01N 1/00
[52] U.S. Cl. .................................................. 73/865.8
[58] Field of Search .............. 73/864.81, 865.5, 865.8, 73/863.21, 863.81, 863.86, 863.83; 198/339.1; 358/106, 107; 356/335, 336, 445

[56] References Cited

U.S. PATENT DOCUMENTS

| | | | |
|---|---|---|---|
| 2,353,828 | 7/1944 | Hyde | 73/863.21 |
| 3,596,839 | 8/1971 | Putman | 241/21 |
| 3,719,089 | 3/1973 | Kelsall et al. | 73/865.5 |
| 3,739,180 | 6/1973 | Carlson | 73/865.5 |
| 4,371,081 | 2/1983 | Satake | 209/580 |
| 4,976,540 | 12/1990 | Kitamura et al. | 356/445 |

FOREIGN PATENT DOCUMENTS

| | | | |
|---|---|---|---|
| 0164331 | 12/1980 | Japan | 73/865.8 |
| 0279138 | 11/1988 | Japan | 73/865.5 |
| 1385033 | 3/1988 | U.S.S.R. | 73/865.5 |
| 1140819 | 1/1969 | United Kingdom | 73/863.83 |

*Primary Examiner*—Robert Raevis
*Attorney, Agent, or Firm*—Bauer & Schaffer

[57] ABSTRACT

An apparatus for inspecting powder granule sample having a sampler for continuously sampling powder granules from an on-line tube by a predetermined amount of a cyclone for separating sample powder granules from air a conveyor tube obliquely located and communicated at its upper end with said cyclone and for conveying sampled powder granules from the cyclone downward, a transfer tube for transferring the sampled powder granules from a lower end opening of the conveyor tube to the on-line tube, an inspector for inspecting the sampled powder granules within the conveyor tube, and adjuster for adjusting the amount of the sampled powder granules within the conveyor tube.

8 Claims, 5 Drawing Sheets

POWDER GRANULE SAMPLE INSPECTION APPARATUS

BACKGROUND OF THE INVENTION

1. Field of the Invention

The present invention relates generally to powder granule sample inspection apparatuses that automatically and continuously inspect the number and size of coloured foreign particles mixed into the powder granule samples that are continuously sampled from an on-line tube or the like.

2. Description of the Prior Art

In order to inspect the number, size and so on of coloured foreign particles mixed into the powder granules such as pharmaceutical items and plastic material or the like that flow inside the on-line tube, according to the prior art, at every time when such inspection is necessary, powder granules are sampled by manually inserting such sampling tool into the on-line tube and then manually inspected. Accordingly, the inspection consumed hand work and much time, where the sample would change characteristics thereof during the inspection so that the acquired inspection data was of inferior precision. Further, since the inspection was only conducted on the obtained sample at each time, the acquired data was such that it can be said not to accurately reflect the nature of the sample that is continuously flowing through the on-line tube.

OBJECTS AND SUMMARY OF THE INVENTION

Therefore, it is an object of the present invention to propose a powder granule sample inspection apparatus that can continuously and automatically inspect the number and size of the coloured foreign particles that are mixed in the powder granule that is continuously sampled from the on-line tube.

According to an aspect of the present invention, there is provided an apparatus for inspecting powder granule sample, comprising:
a) sampling means for continuously sampling powder granules from an on-line tube by a predetermined amount;
b) a cyclone for separating sampled powder granules from air;
c) a conveyer tube obliquely located and communicated at its upper end with said cyclone and for conveying sampled powder granules from said cyclone downward;
d) transfer means for transferring said sampled powder granules from a lower end opening of said conveyer tube to said on-line tube;
e) inspection means for inspecting said sampled powder granules within said conveyer tube; and
f) adjusting means for adjusting the amount of said sampled powder granules within said conveyer tube.

The additional, and other objects, features and advantages of the present invention will become apparent from the following description taken in conjunction with the accompanying drawings in which the same reference numerals designate same and similar parts and elements.

DESCRIPTION OF THE PREFERRED EMBODIMENTS

The present invention will be explained hereunder in reference with the drawings.

Figure 1:
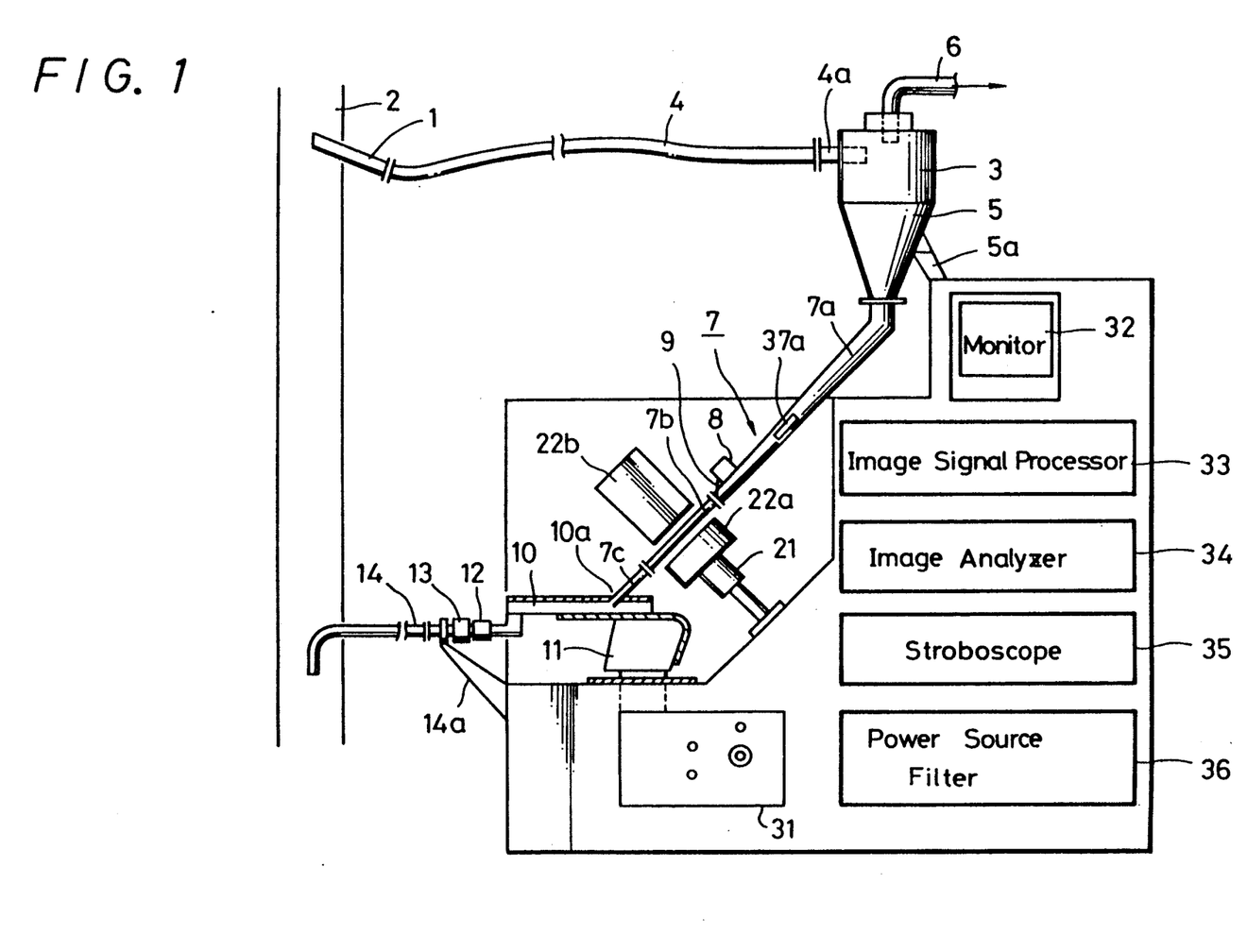
FIG. 1 is a partial vertical sectional diagram showing a first embodiment of the powder granule sample inspection apparatus according to the present invention.

FIG. 1 shows a partial vertical cross-sectional view showing a first embodiment of the powder granule sample inspection apparatus according to the present invention.

Referring to FIG. 1, 1 is a sampling nozzle that samples the powder granules (such as polyvinyl chloride pellets or the like) from an on-line tube 2, which uniformly samples the powder granules that flow along with an air current inside the on-line tube 2 by a predetermined volume continuously. 3 is a cyclone which separates the powder granule samples from air which are sampled and fed through a sample transfer tube 4 with the air flow thereto. This cyclone 3 is installed to be communicated with the upper opening of hopper 5. The hopper 5 is supported and secured to the upper part of the apparatus through a support column 5a. Sample transfer tube 4 is connected to the side of cyclone 3 via a blow out nozzle 4a. Also, an air blow out tube 6 is connected to the upper part of cyclone 3.

From the lower bottom outlet of hopper 5, a conveyer tube 7 is installed to extend downwards at an inclined angle with its outlet positioned on top if trough 10. Conveyer tube 7 consists of a first tube portion 7a which is communicated to the outlet mouth of hopper 5, a second tube portion 7b which is connected thereto, and a 3rd tube portion 7c which is connected thereto and has its outlet mouth positioned above the trough 10.

The first tube portion 7a is made of, for example, stainless steel with a square cross section, which gradually becomes thinner where the tube diameter in the longitudinal or vertical direction at the connection part to tube portion 7b is of such size that one piece of the samples will easily pass, for instance, in this case, is about 1.5–3 times the granule diameter of the sample, and the tube length in the lateral or, horizontal direction is of a size that a plurality of samples will lineup and pass, for instance, in this case, is slightly larger than 4 times the granule diameter of the sample. Also, the lateral length of the tube 7b may be of such size that the sample will pass in single row. Also, static electricity remover 8 that removes the static electricity of the samples that pass the tube 7a is installed in connection therewith because if the static electricity is not removed from the samples, they become a large block and hence they become difficult to flow through the conveyer tube 7 and to clog the same. Near the static electricity remover 8, a layer thickness adjuster 9 which spreads the samples that pass the tube 7a into a single layer is installed adjacent to its connecting portion with tube portion 7b.

Figure 2:
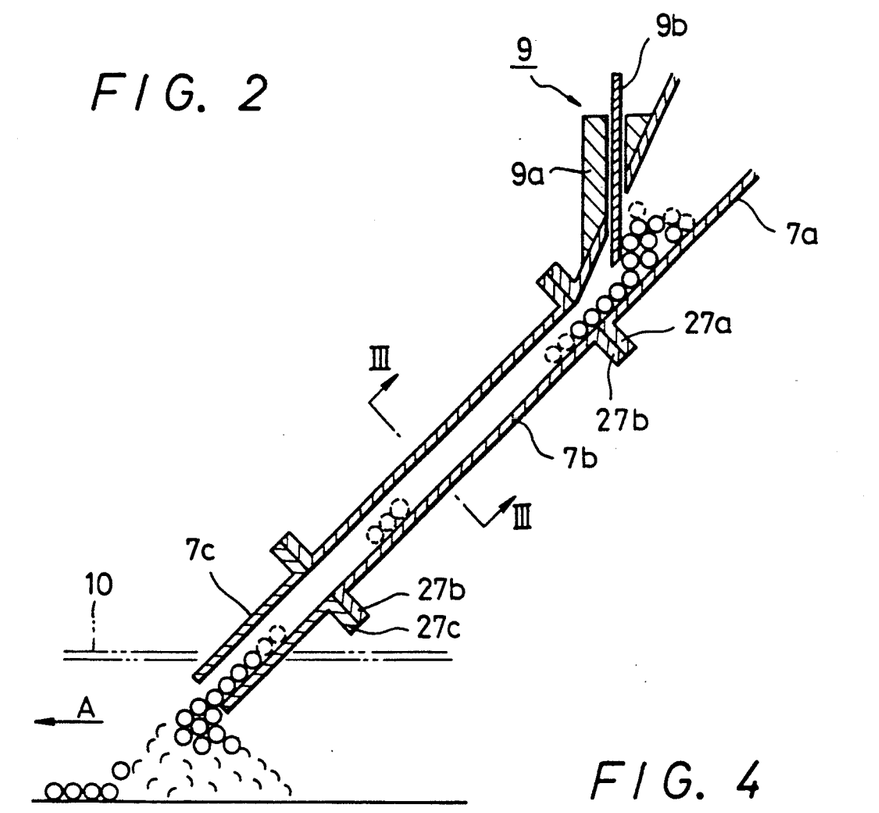
FIG. 2 is an enlarged view showing its important portion.

As shown in FIG. 2, layer thickness adjuster 9 consists of slide gate 9b that is perpendicularly inserted inside tube portion 7a which freely can slide against support portion 9a that is secured to the outer wall of tube portion 7a. The slide gate 9b at the inserted portion into tube portion 7a has generally the same width to the sidewise length of tube portion 7a, and the layer thickness adjuster 9 spreads the samples into a single layer by setting the distance between the lower edge of slide gate 9b and the lower side wall of tube portion 7a to a predetermined value. Further, a peep hole window 37a is provided at tube portion 7a in order to peep at the sample inside the tube 7a.

Figure 3:
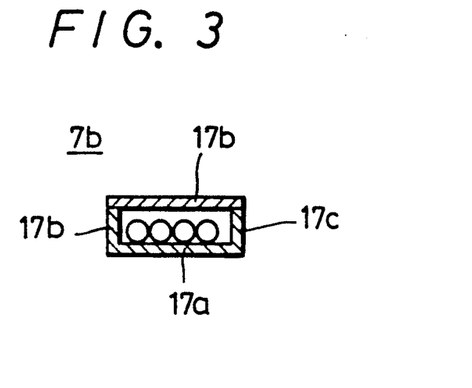
FIG. 3 is a cross-sectional view of the line III—III in FIG. 2.

The second tube portion 7b is made of glass or transparent plastic material, and is of a square cross section as shown on FIG. 3 which is the III—III line cross section of FIG. 2, in which a lower wall 17a and both side walls 17b, 17c are formed as one body where a top wall 17d is secured to the walls 17b, 17c to cover the same from above. The tube portion 7b is connected with tube portions 7a, 7c by respectively fixing flanges 27b and 27b provided at both ends of the portion 7b to flanges 27a and 27c that are installed at the ends of tube portions 7a, 7c through bolts (not shown). The third tube portion 7c is made of stainless steel similar to tube portion 7a and has a square cross section. Also, the tube sizes of tube portions 7b, 7c are the same tube size of the connection part between tube portion 7a and tube portion 7b.

Trough 10 is a cylindrical-shaped body with a square cross section where the bottom surface and side surfaces are formed as separate bodies. The outlet mouth of the third tube portion 7c protrudes through a hole portion 10a that is formed through the upper surface of trough 10 so that it is located at a distance with the bottom surface of trough 10 that is about a few times of the sample granule diameter, as shown in FIG. 2. Under trough 10, a magneto coil 11 is installed to provide vibration in trough 10, whereas by the vibration provided from magneto coil 11, as shown on FIG. 2, trough 10 will cutout a constant volume of the samples that are collected on its bottom surface to move cutout samples in the direction as indicated by arrow A in FIG. 2.

Also, as shown in FIG. 1, trough 10 is connected to transfer tube 14 via elastic tube 12 and ejector 13. Transfer tube 14 is secured to the side of the apparatus by support column 14a and is connected to the on-line tube 2. Elastic tube 12 is provided with a purpose to prevent the vibration of trough 10 to be transmitted to transfer tube 14 and ejector 13 is provided to generate an air flow towards on-line 2 at the inside of transfer tube 14.

As shown in FIG. 1, a television camera 21 is installed at the underside of second tube portion 7b along the same and photosenses the entire samples that move within the tube portion 7b. Further, strobo light sources 22a, 22b are provided that intermittently irradiate the entire samples within tube portion 7b and are positioned at the upper and under sides of tube portion 7b respectively.

In FIG. 1, 31 is a vibration controller which adjusts the vibration force applied from magneto coil 11 to trough 10 in order to set the cutout volume by the trough 10 so that the samples are steadily existing at the entire second tube portion 7b, 32 is a monitor which displays an image based upon the video signal from television camera 21, 33 is an image signal processor, and 34 is an image analyzer, whereas such equipments are used for the image analysis of the image signal from the television camera 21 so that judgement is made on the number and size of the coloured foreign particles mixed into the sample and so on. 35 is a stroboscope main unit that controls the cycle, etc., of strobo light sources 22a and 22b, and 36 is a power source filter that adjusts the power source.

As the next step, the operation of the first embodiment of the present invention will be explained.

The powder granules that flow in the on-line tube 2 are uniformly sample from the entire flow in a predetermined volume continuously by the sampling nozzle 1, pass through the transfer tube 4 with the airflow, and are sent to cyclone 3. The samples are blown into cyclone 3 from the blow out nozzle 4a and are separated from the air while circulating inside cyclone 3. The air is exhausted from the air outlet hose 6. The separated samples drop into the first tube portion 7a while slightly accumulating in hopper 5, and slides downwards along the under side wall of tube portion 7a.

The static electricity of transferred samples inside tube portion 7a is removed by the static electricity remover 8 and then the samples are spread into a single layer by the layer thickness adjuster 9. For such reason, a slight accumulation of the samples in the tube portion 7a occurs upstream of the layer thickness adjuster 9.

The single layered samples line up in 4 rows in this example, and slide downwards as they are along the lower wall of the second tube portion 7b, as shown in FIG. 3. At this time, the samples inside the tube portion 7b are intermittently irradiated from both sides by strobo light sources 22a and 22b and then photosensed by the television camera 21, to measure the number and size of the coloured foreign particles mixed into the samples.

The samples that have moved inside the second tube portion 7b, further move inside the third tube portion 7c, drop on the bottom surface of trough 10 and accumulates thereon in the condition as shown on FIG. 2. At such time, the samples inside tube portion 7c will show a status as held against the accumulated samples at its outlet portion.

The samples that accumulate on the bottom surface of trough 10 are cut out at a predetermined volume by the vibration transmitted thereto from magneto coil 11, sent in the arrow A direction on FIG. 2, and in conjunction thereto, the samples inside conveyer tube 7 shall move downwards to accumulate on the bottom surface of trough 10. In other words, the samples cutout by trough 10 and the sample movement within the conveyer tube 7 are ganged to each other. At this time, the strength of the vibration by the magneto coil 11 is adjusted to a strength so that no portion in the tube portion 7b will be without sample existence by having an excessive cutout volume by trough 10, by looking through the peep window 37a and adjusting the vibration adjuster 31 by confirming the existence or not of the sample inside tube portion 7a. Accordingly, there will always be a certain volume of samples inside tube portion 7b.

The samples transferred by trough 10 will be returned into on-line tube 2 by air-flow generated by ejector 13 to pass flexible tube 12, ejector 13 and transfer tube 14.

According to the first embodiment of the present invention, as described above, the continuously sampled powder granule samples will be photosensed by television camera 21 while being transferred within tube portion 7b and thereafter are returned to on-line tube 2, so that the number and size or the like of coloured foreign particles mixed into the powders can be continuously and automatically inspected. Therefore, the inspection data that accurately reflect the characteristics of the powder granules that continuously flow inside the on-line tube 2 can be made available.

Further, in view of such continuous and automatic inspection operation, manpower is not necessary and inspection data with high precision can be obtained. Especially, the samples inside tube portion 7b will move along its wall at the side of television camera 21 upon being in a condition as a single layer by the layer thickness adjuster 9, whereby there will be no invisible sample by an overlay, and the entire samples will be photosensed at even distance by the television camera 21, with a further regular existence of samples in certain volume within tube portion 7b, the coloured foreign particle content in the sample can be grasped steadily at the same sample volume to make a uniformed inspection so that the inspection data will be of high precision.

Further, the sampled powder granule samples are inspected in a relatively short period of time, that is to say, during a period of time in which the powder granules are sampled by sampling nozzle 1, separated and collected in cyclone 3 and are moving along the inside of tube portions 7a, 7b, so that the samples are not changed in nature and a further high precision inspection data can be obtained.

Also, since the samples after the inspection are returned to on-line tube 2, loss of the powder granules flowing through one-line tube 2 due to inspection can be prevented.

Figure 4:
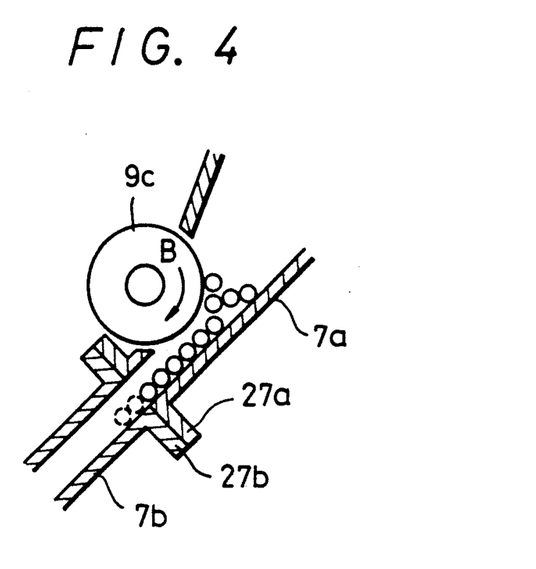
FIG. 4 is a vertical sectional view showing a modified example of the layer thickness adjuster shown in FIG. 1.

As a modified example of the present invention, the layer thickness adjuster 9 can be formed of rotary roller 9c as shown on FIG. 4. The rotary roller 9c will be constantly rotating in the arrow B direction which will make a setup of distance between the bottom wall of tube portion 7a and the roller 9c in a predetermined value in the same manner to the above mentioned example of the present invention. This will allow to spread the samples in a single layer same as the above example.

A second embodiment of the present invention will be described with reference to FIGS. 5 to 7.

Figure 5:
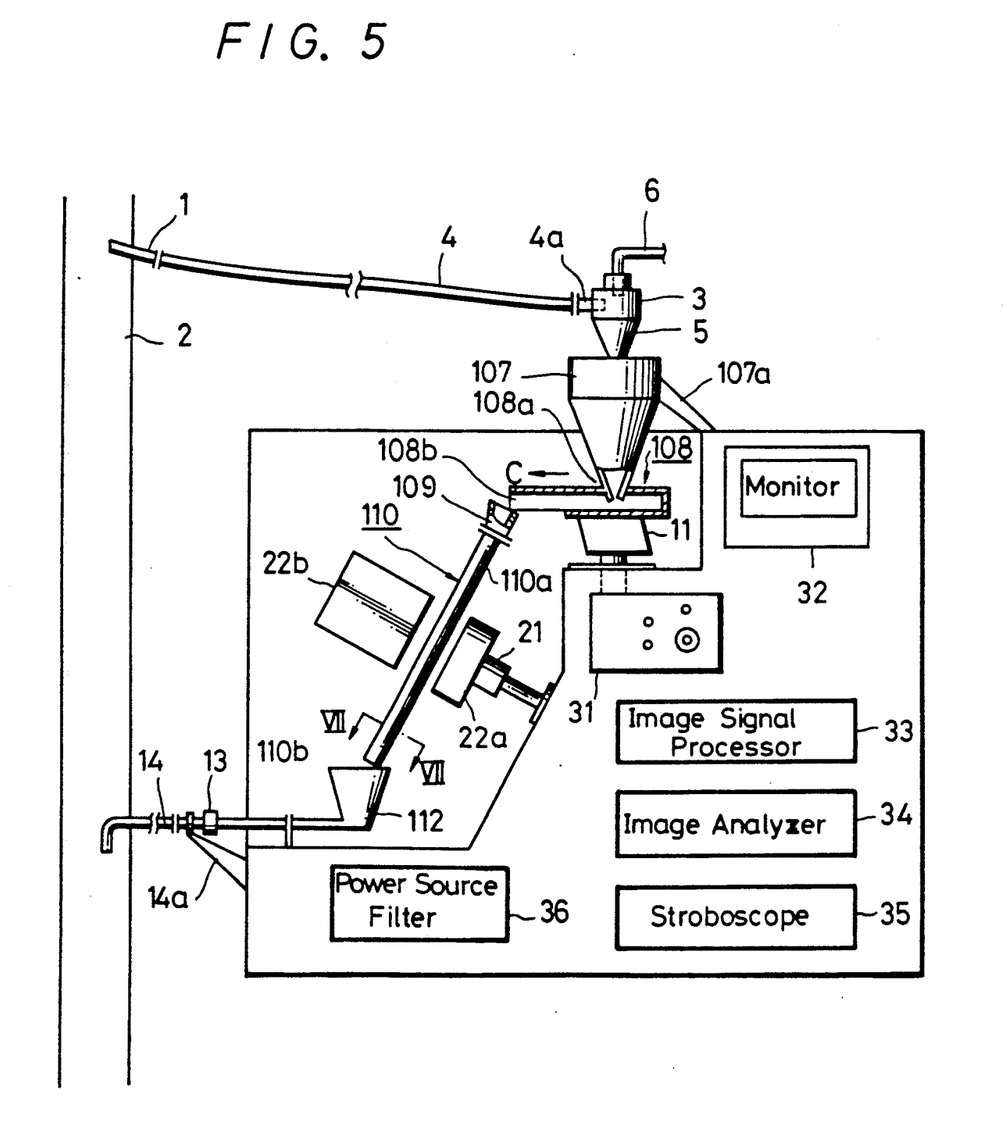
FIG. 5 is a partial vertical sectional view showing a second embodiment of the present invention.

FIG. 5 shows generally the second embodiment of the present invention in which the references same as those of FIG. 1 designate the same or similar elements and parts and their detailed explanation will be omitted.

In the second embodiment of the present invention, as shown in FIG. 5, the samples separated by cyclone 3 and fallen through hopper 5 are accumulated within a material hopper 107. The material hopper 107 is supported and fixed to the apparatus by a support column 107a above the same.

Beneath the outlet of hopper 107 provided at its bottom there is located trough 108, which is substantially similar to the trough 10 of the first embodiment in structure and operation. In this case, the outlet of hopper 107 is inserted into the trough 108 through an opening 108a formed through the upper wall of trough 108 with a distance from the bottom wall of trough 108 several times of the diameter of samples as shown in FIG. 6. An outlet 108b of trough 108 is positioned above an opening of guide portion 109 communicated with an upper end opening 110a of a downwardly-inclined conveyer tube 110 whose lower end opening 110b is located above the opening of a receiving hopper 112.

Figure 7:
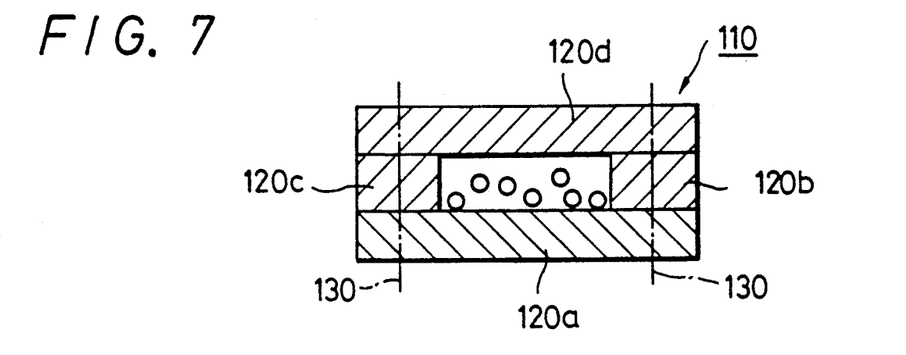
FIG. 7 is a cross-sectional view along the line VII—VII in FIG. 5.

As shown in FIG. 7 which is a cross-sectional view on the line VII—VII in FIG. 5, the conveyer tube 110 has a rectangular cross-section which is formed by bonding its lower wall 120a, its both side walls 120b, 120c and its upper wall 120d by bolts 130 (only center axes thereof are shown in FIG. 7). In that case, the lower wall 120a is made of transparent material, for example, glass but the other walls 120b, 120c and 120d are made of synthetic resin material, for example, opal glass. The outlet of hopper 112 is communicated with on-line tube 2 through ejector 13 and conveyer tube 14.

Figure 6:
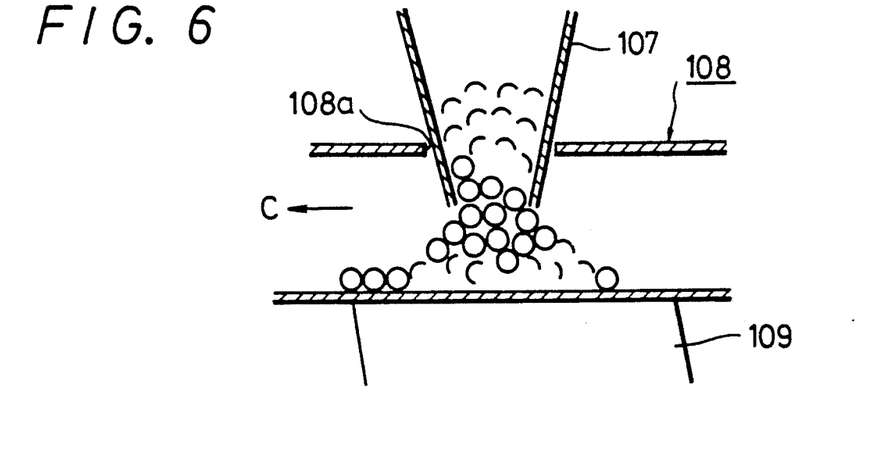
FIG. 6 is a cross-sectional view showing a main portion of the second embodiment in an enlarged scale.

The other construction of the second embodiment of the present invention shown in FIGS. 5 to 7 is substantially same as that of the first embodiment shown in FIGS. 1 to 3.

According to the second embodiment of the present invention, the samples separated from the air by cyclone 3 are fallen into material hopper 107 while accumulated in hopper 5 little and accumulated in hopper 107 under the state that they lie on the bottom wall of trough 108.

The samples lain on the bottom wall of trough 108 are transferred in the direction indicated by an arrow C (see FIG. 6) at a predetermined amount each by the vibration applied thereto from magneto coil 11. In other words, the samples accumulated in material hopper 107 are cut and transferred at a predetermined amount each by magneto coil 11. At this time, the samples within hopper 107 are moved down and then accumulated on the bottom wall of trough 108.

The samples transferred from trough 108 are fallen through its outlet 108b into guide 109, moved through conveyer tube 110 along its lower wall 120a and then fallen into hopper 112. Since the samples are moved through conveyer tube 110 as if they fall therethrough, the samples can move smoothly through the conveyer tube 110 without being chocked up.

The inspection for the samples moving through the conveyer tube 110 according to the second embodiment shown in FIG. 5 is substantially same as that by the first embodiment shown in FIG. 1.

A third embodiment of the present invention will be described with reference to FIG. 8 in which reference numerals same as those in FIGS. 1 and 5 designate same and similar elements and parts.

Figure 8:
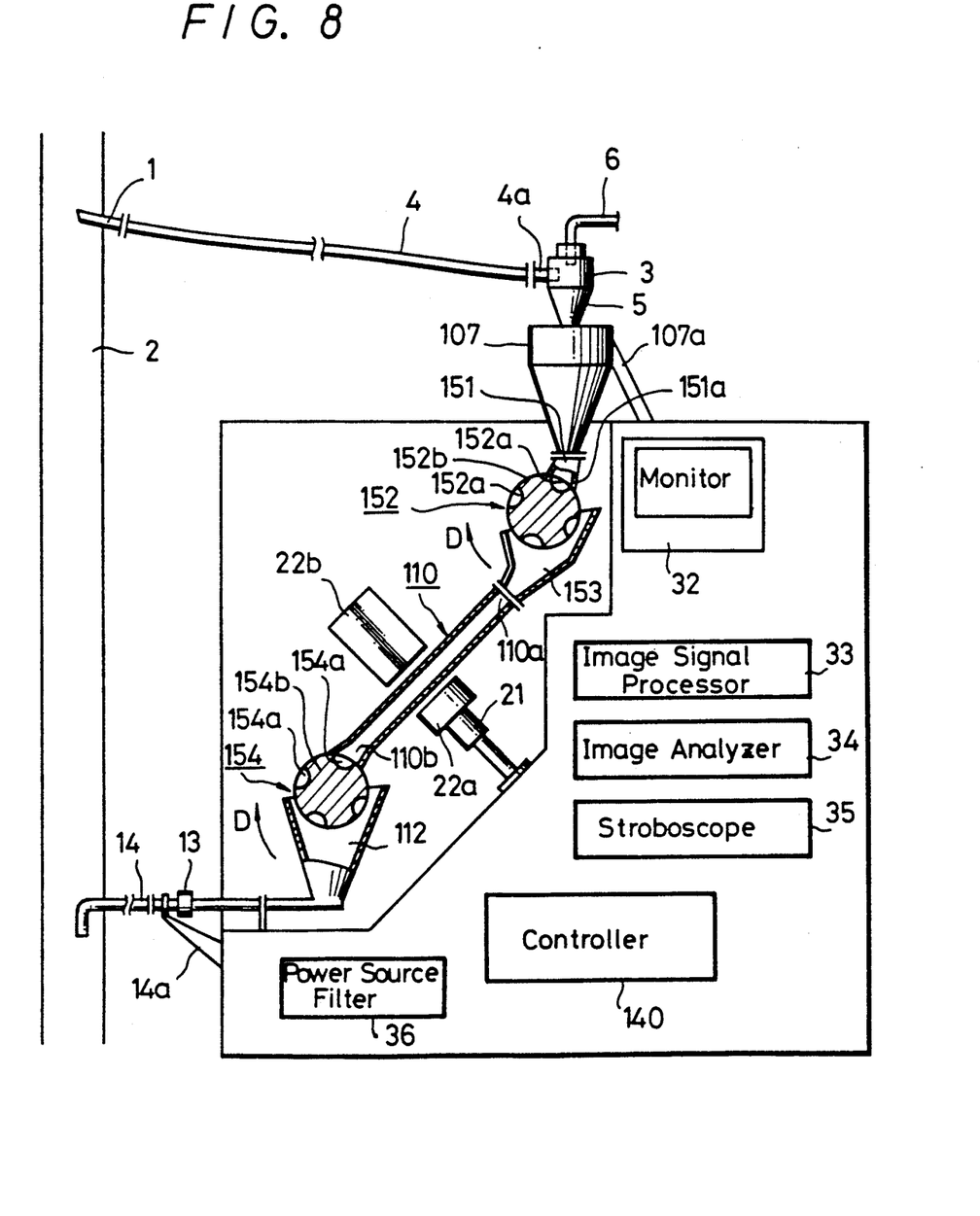
FIG. 8 is a partial vertical sectional view showing a third embodiment of the present invention.

In the third embodiment shown in FIG. 8, the bottom outlet of material hopper 107 is communicated with a first guide member 151 and at the outlet of guide member 151 there is provided a first cutout unit 152.

The first cutout unit 152 is a columnar rotar body which is arranged so that its peripheral surface chokes outlet 151a of the guide portion 151 and rotates. On the peripheral surface of the cutout unit 152 there are formed a plurality of, in this example, four recesses 152a with an equal distance in its circumferential direction. Each of recesses 152a is generally a half spherical shape, and its diameter is smaller than the outlet 151a diameter. Further, the cutout unit 152 is arranged to rotate in the arrow D direction (see FIG. 8) so that its portion facing the outlet 151a shall consecutively be, recess 152a, the neighbouring peripheral surface 152b between adjacent recesses 152a, and recess 152a so that it will cutout the sample from those accumulated in guide 151 and hopper 107 by the amount within recess 152a.

Under the cutout unit 152, a second guide portion 153 is installed so that it will receive the sample as cutout by the cutout unit 152. Guide portion 153 is connected to the entrance 110a of the conveyer tube 110. The outlet 110b of the conveyer tube 110 is formed to be slightly open towards the outside. At the outlet 110b of the conveyer tube 110, a second cutout unit 154 is placed. Cutout unit 154 is of the same construction to cutout unit 152, where each recess 154a has the same volume as that of the recess 152a and its diameter in the circumference direction is formed to be smaller than the diameter of the outlet mouth 110b. Also, with a condition that the circumferential surface of the cutout unit 154 is choking the outlet mouth 110b, it is installed so that its portion in contact with the outlet mouth 110b will consecutively be recess 154a, circumferential surface 154b, recess 154a by an arrow direction D rotation intermittently, so that the sample loaded within the conveyer tube 110 will be cutout by only the volume accumulated in the recess 154a.

A controller 140 has such a control function that under a condition that the samples inside the conveyer tube 110 are loaded at the portion that faces the television camera 21 to be photosensed by television camera 21, the cutout unit 154 is rotated in synchronism with cutout unit 152 so that the portion of the former facing the outlet mouth 110b will consecutively be recess 154a, circumferential surface 154b, recess 154a, which on cutout unit 152, portions that face the outlet mouth 151a of the guide portion 151 shall be the recess 152a, circumferential surface 152b and recess 152a, while it also will make television camera 21 and strobo lights 22a operate.

As the next step, the operation of the third embodiment will be explained. The sample that is separated with air in cyclone 3 will accumulate inside the first guide portion 151 and hopper 107 since the outlet mouth 151a of the guide portion 151 is choked by circumferential surface of cutout unit 152. Also, when the recess 152a faces the outlet mouth 151a, the sample will accumulate in a condition that the sample fills the recess 152a. Then, when the cutout unit 152 rotates, the recess 152a with the sample loaded therein will shift in the arrow D direction from outlet mouth 151a so that the sample loaded in the recess 152a will be dropped into second guide portion 153.

Also, at each time that recess 152a faces outlet mouth 151a, the sample gets loaded into recess 152a so that only the sample loaded in recess 152a is cutout from the sample that is accumulated inside guide 151 and hopper 107 to fall into guide 153. The dropped sample moves downward along the under wall 120a (see FIG. 7) of the conveyer tube 110. The conveyed sample will gradually accumulate from the lower side within the conveyer tube 110 because the outlet mouth 110b of the conveyer tube 110 is closed by the circumferential surface 154b of the second cutout unit 154.

Now it be assumed that, for instance, a proper volume of the sample is accumulated inside the first guide 151 and hopper 107, also the sample is loaded up within the conveyer tube 110 in a range facing the television camera 21 and cutout units 152, 154 are at the condition as shown on FIG. 8 with the sample loaded in recesses 152a, 154a. When the cutout units 152, 154 both rotate in the arrow D direction by the controller 140, the same volume of samples are cutout from the insides of guide 151 and hopper 107 as well as the inside of conveyer tube 110. The sample that is cutout by the first cutout unit 151 will drop within guide 153, and the sample that is cut out by the second cutout unit 154 will drop into hopper 112. And then the outlet mouth 151a of guide 151 is closed by circumferential surface 152b and also the outlet mouth 110b of conveyer tube 110 will be closed by circumferential surface 154b. At such time, the sample within the conveyer tube 110 will not move downwards and will be in a static condition.

At the condition where the outlet mouth 110b is closed by circumferential surface 154b, the television camera 21 and strobo light sources 22a, 22b are activated by the controller 140 so that the sample within the conveyer tube 110 will be photosensed by the television camera 21 and the number and size of the coloured foreign particles contained in the sample will be measured. At this time, the sample photosensed is in static condition, while being packed along the under side wall 120a so that the sample surface adheres closely to the surface of wall 120a. In other words, the sample surface is in a static condition within the focal depth of television camera 21. Also the sample that adheres closely to the wall 120a photosensed is always a constant volume. Accordingly, a regularly predetermined volume of the sample is photosensed by the television camera 21 in good precision. Further, the light irradiated by the strobo light 22b which is at the top side of conveyer tube 110 passes the upper wall 120d to irradiate on the sample where the top side wall 120d is formed by a milky white plastic so that the light is weakend by being diffused by which the shade that is generated by the strobo light 22a on the photosensed sample is favourably erased. Therefore, the sample shade is not erroneously recognized as a coloured foreign particle and such obtained inspection data is increasingly reliable.

When the cutout units 152, 154 will rotate with the result that recess 152a will face the outlet mouth 151a of guide 151 while recess 154a faces outlet mouth 110b of conveyer tube 110, the sample inside the guide 151 and hopper 107 will accumulate in the recess 152a while the sample that is loaded inside the conveyer tube 110 will move down to accumulate in recess 154a. At this time, the sample already photosensed will also move down. On the other hand, when the sample in the conveyer tube 110 is cutout by the cutout unit 154, the same volume of sample that is loaded inside guide 151 and hopper 107 is cutout by cutout unit 152 to be supplied into conveyer tube 110. Therefore, there will be a constant volume of the sample regularly existing inside conveyer tube 110.

Further, it is formed that the volume of recesses 152a, 154a of cutout units 152, 154, namely, the cutout volumes of cutout units 152, 154 are selected to be equal to the volume of the sample photosensed within the conveyer tube 110. Accordingly, the sample photosensed within conveyer tube 110 will be replaced with new sample at each time it is cutout by the cutout unit 154. Thus, the sample that lays along the wall 120a is efficiently photosensed by the television camera 21 so that the inspection efficiency is raised.

Finally, the sample accumulated in hopper 112 is returned to on-line tube 2 via ejector 13 and transfer tube 14 by the airflow that is generated by ejector 13. According to the third embodiment of the present invention, the same advantages and effects achieved by the first and second embodiments are also performed. In addition, in the third embodiment, the sample inside the conveyer tube 110 is choked, it remains in static condition when the cutout unit 154 closes the outlet mouth 110b and further the sample photosensed along the wall 120a is of a predetermined volume with its surface in close adherence to the wall 120a, so that the television camera 21 can favourably photosense the static constant volume sample surface within its focal distance. Therefore, a higher precisioned inspection data can be obtained.

Further, since the sampled powder granule sample is inspected in such relatively short period of time, that is to say, in the period in which the granule is sampled by the sampling nozzle 1, separated at cyclone 3, accumulated inside the guide portion 151 and hopper 107, cutout by the cutout unit 152 and is moved inside the conveyer tube 110 while being choked, the sample is not caused any change in characteristics so that further high precisioned inspection data can be obtained.

Although in the above-mentioned embodiments all the lower wall of conveyer tube is made of transparent glass, such a variation may be possible that the other portion except for its portion facing the television camera 21 can be made of opaque material. Also one of strobo light sources 22a, 22b may be omitted.

Further, in the second embodiment shown in FIG. 5, in place of trough 108 a rotary disc or turntable may be employed. That is, in the second embodiment of FIG. 5, the outlet of hopper 107 is closed to the upper surface of the turntable and this turntable is rotated to move the sample on the turntable little by little and to thereby drop the sample within hopper 107. In this case, the sample on the turntable is fed to the guide 109 after being moved. Also in this case, a motor is used in place of magneto coil 11 to rotate the turntable and a speed adjuster is employed instead of vibration adjuster 31 to adjust the rotation speed of the motor.

Figure 9:
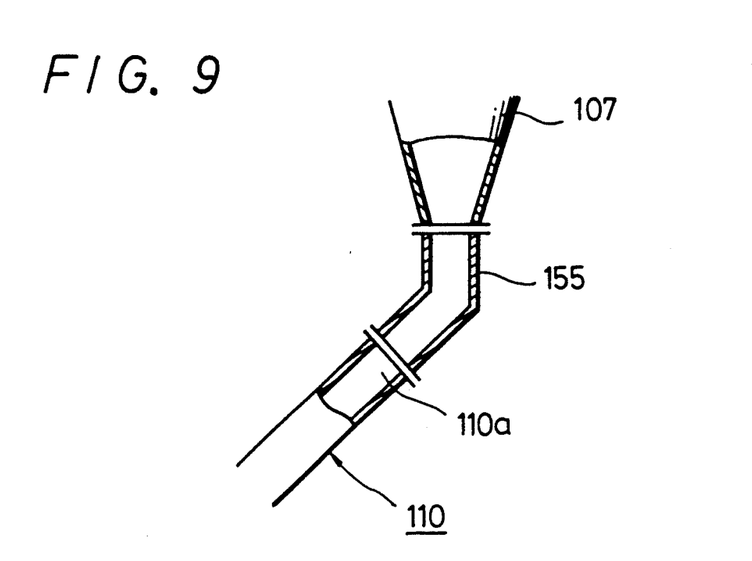
FIG. 9 is a partial cross-sectional view showing a main portion of a modified embodiment of the third embodiment of the present invention.

Furthermore, in the third embodiment shown in FIG. 8, the first cutout unit 152 may be omitted. In this case, as shown in FIG. 9, the lower outlet of hopper 107 is directly communicated with the inlet 110a of conveyer tube 110 via a communication tube 155. In that case, in order to avoid that the sample within the conveyer tube 110 overflows its inlet 110a and the sample photosensed by the television camera 21 disappears, there may be provided means for adjusting the sampling amount by the sampling nozzle or means having variable apertures or slits to pass therethrough always a constant amount of samples in the hopper 107 are provided at its outlet.

It will be apparent that many modifications and variations could be effected by one skilled in the art without departing from the spirits or the scope of the novel concepts of the present invention so that the spirits or scope of the present invention should be determined by the appended claims only.

I claim as my invention:

1. Apparatus for inspecting powder, granular, and particulate specimens, comprising means for pneumatically removing a sampling of said specimens from an in-line processing system; a cyclone for separating the specimens in said sample from the air, said cyclone having an outlet at its lower end through which said specimens pass; a conveyor tube extending downwardly from the outlet of said cyclone, said conveyor tube extending obliquely to permit the sampled specimens to slide downwardly on the inner surface thereof; means located along said oblique conveyor tube for inspecting said sample specimens while said specimens are within said conveyor tube; and means upstream of said inspection means for adjusting the amount of sample specimens moving within said conveyor tube, said means comprising a gate inserted within the wall of said conveyor tube and being adjustable in cooperation with the surface of said tube to arrange said sample specimens into a single layer.

2. The apparatus according to claim 1, wherein the adjustment means comprises a slideable plate mounted within said tubular conduit upstream of said rectangular portion, said plate being adjustable to define the space with respect to the surface of said tubular conduit to permit only a single layer of said granules to pass.

3. The apparatus according to claim 1, wherein he adjustment means comprises a rotary gate mounted within said tubular conduit upstream of said rectangular portion, said rotary gate having at least one groove on its surface for receiving a single layer of granules, said rotary gate being rotatable to deposit said single layer on the surface of said rectangular portion.

4. Apparatus for inspecting samples of powder granules flowing in an in-line processing system comprising pneumatic means for continuously removing predetermined amounts of said granules from said in-line processing system; cyclone means for separating the granules from the air in which said granules are removed; a tubular conduit extending at an oblique angle downwardly from the outlet of said cyclone means through which said granules fall; transfer means for returning said granules from said tubular conduit to said in-line processing system; and sensing means for inspecting the granules as they pass through said tubular conduit arranged on the exterior of said tubular conduit, said tubular conduit located in proximity to said sensing means being rectangular in cross section and transparent to said sensing means; means for adjusting the amount of said granules passing said transparent portion to create a single layer of said granules facing said sensor for inspection.

5. The apparatus according to claim 4, including a light source for illuminating said rectangular portion and a television camera located to sensing said granules through said transparent wall.

6. The apparatus according to claim 5, including an image processor for processing a video signal from said television camera to detect a number and a size of foreign particles mixed into said sampled powder granules.

7. The apparatus according to claim 6, including a monitor for displaying an image of said sampled powder granules on the basis of a video signal from said television camera.

8. The apparatus according to claim 4, including means for removing static electricity from said granules within said tubular conveyor.

* * * * *